(12) United States Patent
Kraemer

(10) Patent No.: US 10,925,769 B2
(45) Date of Patent: Feb. 23, 2021

(54) SURGICAL INSTRUMENT FOR MINIMALLY INVASIVE ASPIRATION OF TISSUE

(71) Applicant: Light Matter Interaction Inc., Toronto (CA)

(72) Inventor: Darren Kraemer, Toronto (CA)

(73) Assignee: Light Matter Interaction Inc., Toronto (CA)

( * ) Notice: Subject to any disclaimer, the term of this patent is extended or adjusted under 35 U.S.C. 154(b) by 138 days.

(21) Appl. No.: 16/137,894

(22) Filed: Sep. 21, 2018

(65) Prior Publication Data

US 2019/0091067 A1 Mar. 28, 2019

Related U.S. Application Data

(60) Provisional application No. 62/564,019, filed on Sep. 27, 2017.

(51) Int. Cl.
*A61F 9/008* (2006.01)
*A61F 9/009* (2006.01)
(Continued)

(52) U.S. Cl.
CPC .......... *A61F 9/00834* (2013.01); *A61F 9/009* (2013.01); *A61F 9/00821* (2013.01); *A61F 9/00825* (2013.01); *A61B 17/00234* (2013.01); *A61B 18/22* (2013.01); *A61B 2018/00577* (2013.01); *A61B 2018/00642* (2013.01); *A61B 2018/00732* (2013.01); *A61B 2018/00863* (2013.01); *A61B 2018/2005* (2013.01); *A61B 2218/002* (2013.01); *A61B 2218/007* (2013.01); *A61F 2009/0087* (2013.01); *A61F 2009/00872* (2013.01); *A61F 2009/00887* (2013.01); *A61F 2009/00897* (2013.01)

(58) Field of Classification Search
CPC .............. A61F 9/00834; A61F 9/00825; A61F 9/00821; A61F 9/009; A61F 2009/00887; A61B 18/22; A61B 2018/00642
See application file for complete search history.

(56) References Cited

U.S. PATENT DOCUMENTS

| 6,471,692 | B1 * | 10/2002 | Eckhouse | ............ A61N 5/0601 606/15 |
| 2002/0013572 | A1 * | 1/2002 | Berlin | ..................... A61F 9/008 606/4 |

(Continued)

OTHER PUBLICATIONS

Anderson "Sapphire Optical Fibers Better Than Silica Fibers?" Tech Fragments https://techfragments.com/sapphire-optical-fibers/ Published Aug. 14, 2012, Accessed Mar. 18, 2020 (Year: 2012).*

*Primary Examiner* — Nathan J Jenness

(57) ABSTRACT

An apparatus for disruption of cataracts in lens tissue. The apparatus includes a housing; a source of pulsed laser radiation; and an optical waveguide. The optical waveguide is configured to transmit the pulsed laser radiation from the source of pulsed laser radiation, and is coupleable to the source of pulsed laser radiation at a proximal end of the optical waveguide to receive the pulsed laser radiation from the source of pulsed laser radiation. The apparatus also includes a driving mechanism coupled to the optical waveguide for controllably changing the position of the optical waveguide relative to a distal end of the housing.

13 Claims, 3 Drawing Sheets

(51) Int. Cl.
*A61B 17/00* (2006.01)
*A61B 18/00* (2006.01)
*A61B 18/20* (2006.01)
*A61B 18/22* (2006.01)

(56) References Cited

U.S. PATENT DOCUMENTS

2003/0003594 A1* 1/2003 Ogura .................. G01N 21/253
  436/172
2009/0171326 A1* 7/2009 Hohla ................. A61F 9/00736
  606/6

* cited by examiner

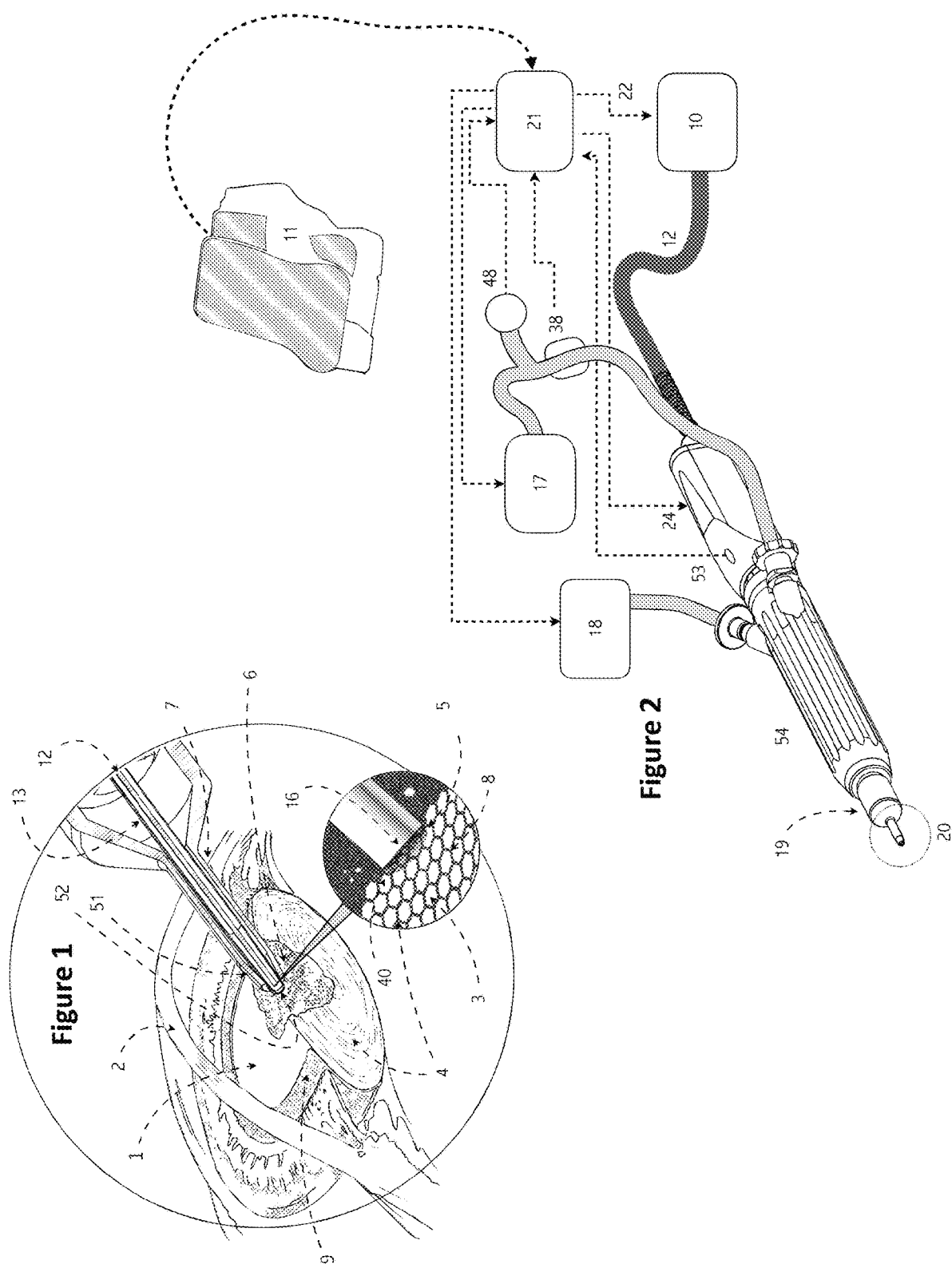

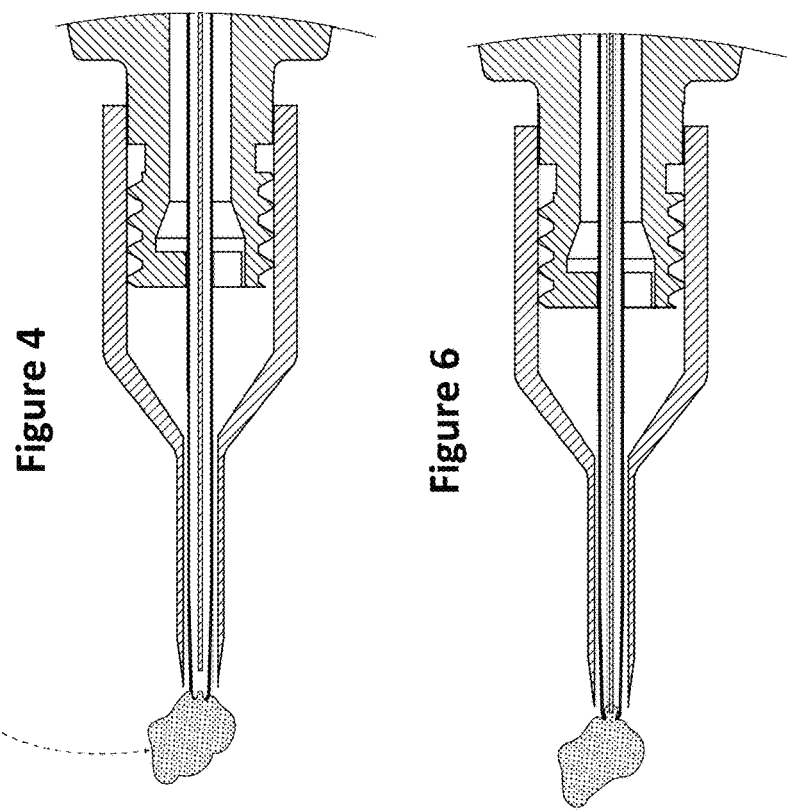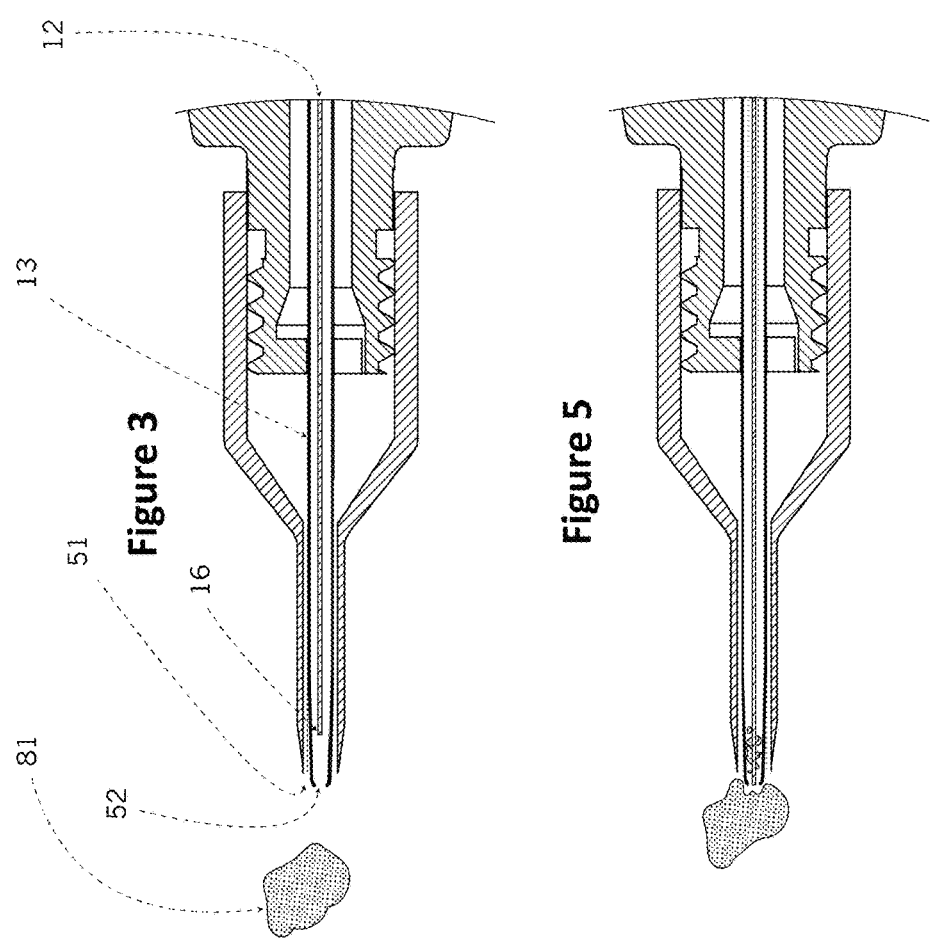

SURGICAL INSTRUMENT FOR MINIMALLY INVASIVE ASPIRATION OF TISSUE

CROSS-REFERENCE TO RELATED APPLICATIONS

The present disclosure claims priority from U.S. provisional patent application No. 62/564,019, filed Sep. 27, 2017, entitled "SURGICAL INSTRUMENT FOR MINIMALLY INVASIVE ASPIRATION OF TISSUE", the entirety of which is hereby incorporated by reference.

FIELD

The present disclosure relates generally to an apparatus and method for use in cataract surgery. Particularly, the present disclosure relates to a surgical laser ablation device and method for disruption and aspiration of cataractous lens tissue.

BACKGROUND

Cataract surgery was developed to treat blindness caused by opacification of lens tissue in the human eye. Although most cases of cataract are related to the aging process, occasionally children can be born with the condition, or a cataract may develop after eye injuries, inflammation and some other eye diseases. Treatment for cataractous lens tissues is one of the most frequently performed surgeries.

In modern small incision cataract surgery, the eye surgeon uses a hand-held metal or diamond blade to create an incision in the area where the sclera meets the cornea. The next step for the cataract surgery is to remove the front portion of the capsule to allow access to the cataract. Once the capsule is opened an instrument can be inserted to break apart and disrupt the cataract prior to removal. Tools for breaking apart the lens include mechanical tools such as 'chopper' or forceps to tear the tissue apart, and more recently tools containing ultrasonic transducers have been used to emulsify tissue prior to aspiration. Various single use ultrasonic aspiration needles have been proposed e.g. U.S. Pat. No. 8,454,551 B2

Devices have been proposed that use laser radiation to break-down tissue through heating effects or acousto-optically generated ultrasonic energy (e.g. U.S. Pat. No. 6,083, 192 A). Additional techniques have been adopted in which radiation from very short pulsed lasers that are not absorbed well in eye tissue are focused inside the volume of the cataractous lens to achieve photo-disruption of the tissue prior to aspiration. This latter technique suffers from the necessity of a projection system, and has not been implemented in a hand-held instrument due to a lack of effective optical waveguide beam delivery for such short pulses.

Microsecond and longer pulsed Mid-IR lasers had been used for ablation of lens tissue. A mechanism for laser ablation (impulsive heat deposition) was described in U.S. Pat. No. 8,029,501 (which is incorporated herein by reference in its entirety) in which rapid-heating by excitation of vibrational modes inside of tissue causes vaporization of the exposed tissue. This laser source required for this new mechanism is compatible with specific fiber optic beam delivery systems.

A surgical apparatus and method in which the laser mechanism described above could be used to disrupt and remove lens tissue via a handheld instrument that included a fiber optic beam delivery system for on contact tissue disruption has been proposed, see WO2016041086A1, the entirety of which is hereby incorporated by reference. In one embodiment of that disclosure, the distal end of the fiber optic was delivered to the tissue inside an aspiration needle of larger diameter.

SUMMARY

In some examples, the present disclosure describes an apparatus for disruption of cataracts in lens tissue. The apparatus includes a housing; a source of pulsed laser radiation; and an optical waveguide. The optical waveguide is at least partially housed within the housing, and includes a flexible optical fiber. The optical waveguide is configured to transmit the pulsed laser radiation for causing disruption of cataracts, and is coupleable to the source of pulsed laser radiation at a proximal end of the optical waveguide to receive the pulsed laser radiation from the source of pulsed laser radiation. The apparatus also includes a driving mechanism coupled to the optical waveguide for controllably changing the position of the optical waveguide relative to a distal end of the housing.

BRIEF DESCRIPTION OF THE DRAWINGS

Reference will now be made, by way of example, to the accompanying drawings which show example embodiments of the present application, and in which:

FIG. 1 is a partial perspective view of an example embodiment of a laser disruption of cataractous lens tissue;

FIG. 2 is a partial perspective view of an example embodiment of a handheld laser instrument that delivers a source of laser pulses;

FIG. 3 is a cross sectional view of an example of a distal tip of the handheld laser instrument of FIG. 2 in which an aspiration needle, and an optical fiber are collinear and an entrance of the aspiration channel is unobstructed;

FIG. 4 is a cross sectional view of an example of a distal tip of the handheld laser instrument of FIG. 2 in which a fragment of tissue is pulled towards the aspiration channel by negative pressure, and is too large to be aspirated and completely occludes an aspiration channel entrance;

FIG. 5 is a cross sectional view of an example of the same tissue fragment of FIG. 4 as it is disrupted and aspirated, and the occlusion is partially or completely cleared;

FIG. 6 is a cross sectional view of an example of a distal tip of the handheld laser instrument of FIG. 2 of a persistent occlusion that occurs in which the laser fiber disrupts all the tissue within its range, but cannot clear the occlusion;

Similar reference numerals may have been used in different figures to denote similar components.

DESCRIPTION OF EXAMPLE EMBODIMENTS

Figure 7:
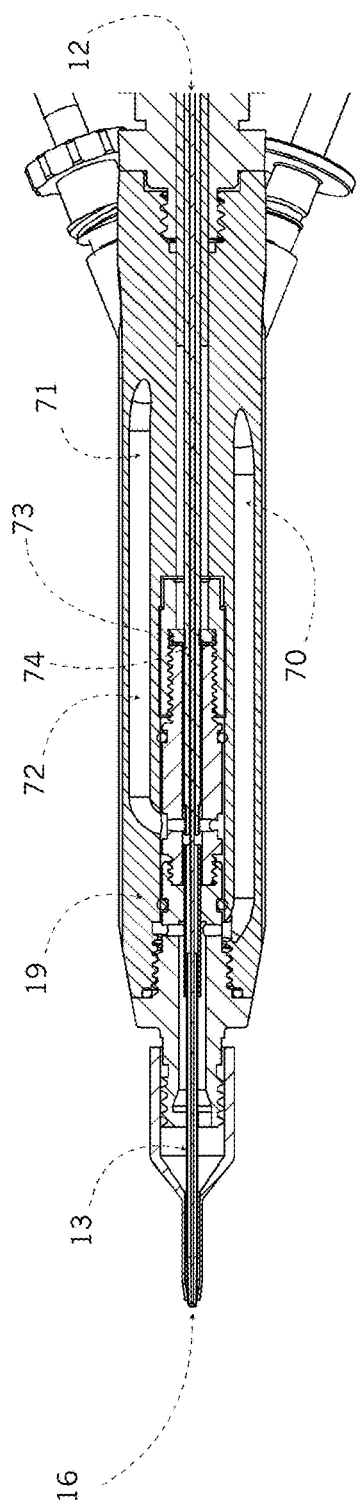
FIG. 7 is cross sectional view of an example handheld laser instrument in which the distal end of the fiber can be set inside the aspiration needle in such a way that the aspirated fluid can be contained within a sterilizable or single use tool assembly and does not contaminate some reusable portion of the fiber optic beam delivery while allowing the non-elastic fiber optic to be moved within the aspiration channel.

In some examples, present disclosure provides a hand held laser phacoemulsification apparatus for disruption and removal of cataractous-lens tissue.

In some examples, the disclosure provides an apparatus that may help to provide improved aspiration rate of a surgical instrument 54, compared to conventional instruments, by utilizing laser energy to disrupt tissue on contact with a fiber optic tip 16. The fiber optic tip 16 sits collinearly within the small diameter of an aspiration channel that is suitable for manually positioning within the anterior capsule of the human eye. The fiber optic 16 is able to advance or retreat within the aspiration channel to enhance the rate of tissue aspiration, and also minimize the risk of disruption to unintentionally aspirated tissue.

In some examples, the disclosure integrates the control of the fluidics (means of aspiration and irrigation) and the laser disruption, with an algorithm that adjusts laser parameters such as pulse rate, envelope and positioning of the laser tip based on user inputs and sensor outputs (e.g., measuring pressure and flow rate within the aspiration and irrigation channels) to achieve faster and more precise aspiration with minimal fluidics (flow and vacuum) and minimal disruption to surrounding tissues.

In some examples, the disclosure provides a surgical instrument 54 in which the user control of aspiration rate is further enhanced by the addition of a moveable fiber optic 16 integrated into the irrigation/aspiration tip and a control system algorithm that, in response to various user inputs and sensed fluidic conditions, automatically optimizes fiber position and laser pulse rate to minimize invasive damage to surrounding tissue structures and limit changes in the pressure of the anterior capsule, as well as minimize the flow of aspiration and irrigation during the tissue removal procedure.

The present disclosure describes an apparatus including a laser probe which, on contact, and internal to the body, can efficiently drive rapid dissolution of tissue by optical excitation of selected vibrational modes inside of the tissue's molecules on timescales faster than heat diffusion to the surroundings. The laser probe uses a laser mechanism similar to that previously disclosed in WO2016041086A1, incorporated by reference herein in its entirety.

This disclosure is directed toward an example approach for efficiently disrupting hard cataract tissue while avoiding the issues of energy propagation into other tissues of the eye.

With reference to FIG. 1, an example laser ablation approach is disclosed. FIG. 1 shows an illustration of laser disruption of cataractous lens tissue 1. The laser disruption occurs when laser pulses of a selected duration, wavelength and pulse energy, such as that disclosed in WO2016041086A1, are coupled to an optical waveguide 12, and exit from the distal end 16 of the optical waveguide 12. The optical wavelength guide 12 has been inserted into the anterior chamber of the eye through an incision point 7 and through an opening in the capsule 9, directed inside of the cataractous lens tissue 1. Light is strongly absorbed by the lens cells 3 or intercellular regions 8, that are in contact with the exit of the waveguide 16 or within a distance close to the optical absorption depth 40 of the laser light inside the tissue irradiates a volume of tissue 5, resulting in disruption of the lens cells and/or the cell structure of the lens 4 and effective dissolution and aspiration of the disrupted fragments of the cataractous tissue 6 with minimal disturbance to distant parts of the eye such as the cornea 2 or the lens capsule 9. A hollow tube or needle 13 provides a means for removal of the disrupted tissue, when connected to a means of vacuum pressure. An inner tip of the aspiration channel 52 contains the distal end of the fiber optic 16 and from which emerge the laser pulses. The laser pulses disrupt the tissue on contact so the resulting material can be aspirated out of the eye.

This collinear delivery of the laser energy is advantageous in the case of small fiber optics and precise laser disruption processes since the tissue is actively drawn towards the laser energy by the aspiration pressure. The on-contact tissue disruption of the current disclosure is not limited to lens tissue and can be applied to all tissue types.

Notably, in an example embodiment, a means to move or reposition the position of the fiber optic tip 16, during the surgical procedure and the means to control this position based on user input and fluidic conditions within the irrigation and aspiration channel is provided, see FIG. 2.

FIG. 2 discloses an example embodiment of the disclosure in which a handheld instrument 54 is coupled to a source of laser pulses 10. The source of laser pulses 10 is controlled by a signal 22 from a control circuit 21 which also controls a means for aspiration 18 and a means for irrigation 17. The source of laser pulses 10 further receives inputs from one or more sensors, such as a flow rate sensor 38 and a pressure sensor 48 within the fluidic channels. The action of irrigation, aspiration pressure, aspiration flow rate and laser power, pulse rate and fiber positioning may further be controlled through the use of a user input device 11 such as a multifunction foot pedal and preset parameters stored within the control circuit 21. Other control means may be provided. The preset parameters may include maximum flow rate and pressure limits, laser power limits and other modes of operation. The irrigation and aspiration channels 52 may be coupled to flexible tubing 100 (see FIG. 8), further coupled to a tool assembly 19, which may be detachable, re-useable or disposable. Flexible tubing 100 allows for insertion and control of the distal tip 20 of the tool assembly 19 inside an ocular lens 1 to achieve controlled micro-disruption of the cataract tissue at the tip, see FIG. 1. In one example, a means 24 (e.g., driving mechanism such as a linear motor, or linear translation mechanism driven by a rotating motor, voice-coil actuator etc.) of moving the optical fiber 12 is provided to control relative distance of the distal fiber optic tip 16 to the distal end of the aspiration channel 52. A sensor or encoder 53 (e.g., photo-acoustics sensor) to track the fiber tip position may be provided. Another sensor may also be provided to detect when there is physical contact between the optical fiber 12 and the tissue.

In some examples, the optical fiber 12 may be made of any suitable material, such as sapphire, diamond, ZBLAN or YAG. The fiber optic tip 16 may be straight, or have any other suitable configuration, for example curved, tapered or angled, such as described in WO2016041086A1.

A user can control the position of the fiber optic tip 16 in a number of different ways. In one example embodiment, an additional user input device configured to move the fiber position forwards or backwards is provided. In a further example, the fiber is advanced using a proportional pedal that is generally used in a conventional procedure to increase the flow rate/aspiration pressure. Actuation of the pedal causes higher levels of aspiration, and at the same time the proximity of the laser disruption mechanism to the aspiration tip is decreased.

In some examples, the position of the fiber tip 16 is automatically adjusted based on the reaction of the pressure and flow rate of the aspiration channel 52 to the user's demands for higher levels of aspiration, for example by sensing a degree of occlusion on the tip. In such an embodiment, the position of the fiber optic tip 16 may be determined directly by the surgeon, or in combination with a control algorithm that senses the fluid conditions within the aspiration channel 52 and identifies several conditions including occlusions and unobstructed flow. In some examples, automatic adjustment may be used in combination with direct user input to control the position of the fiber optic top 16.

In a conventional cataract surgical system the user has control (e.g., via a foot pedal) of aspiration. A conventional system may include some simple automatic controls for limiting the flow if the pressure is too high. In the present disclosure, a more comprehensive control of the system is provided, in which the laser parameters are also controlled while taking into account into the pressure and flow detected, and also while controlling positioning of the optical fiber. For example, the flow may be limited because the pressure is too high, and further the system controls the laser to turn on and controls the optical fiber to move distally towards the tip as a way to decrease the pressure. Further details of such comprehensive control is described below.

With reference to FIG. 3, under unobstructed conditions, the relationship between flow and pressure inside the aspiration channel 52 can be approximated by considering laminar flow and a Newtonian fluid inside a circular cross section pipe, by considering laminar flow according to Poiseuilles law:

$$Q = \frac{\pi R^4}{8\eta L}\Delta p$$

where $$Q = \frac{dV}{dt}$$

is the volumetric flow rate (volume/time), $\Delta p$ is the change in pressure across both ends of the pipe, R, the radius of the pipe and $\eta$ is the viscosity of the fluid, and L the length of the pipe. As disclosed by Poiseuille's equation, for rising viscosity, a larger pressure difference is required to maintain a constant flow rate. To prevent catastrophic pressure changes from damaging the eye, most opthlalmological aspiration devices have a configurable pressure limit, $\Delta p_{max}$, often set to around 350-600 mm/hg. Above this pressure, the pump is prevented from working harder and the flow rate is thus prevented from increasing. Similarly, there is often a flow rate limit as well, $Q_{max}$ set around 20-50 cc/min for the purposes of aspirating tissue.

Given a user control signal for desired aspiration flow rate, which can vary from 0-100%, the user could expect the flow to follow the control signal up to the maximum pressure.

$Q \propto A(\Delta p)$ for $\Delta p < \Delta p_{max}$ or $Q \propto A(\Delta p_{max})$ With limited pressure it is important to consider ways to prevent high viscosity tissues from blocking the aspiration channel 52. For example, to minimize clogging downstream, the tip 51 of the aspiration channel 52 can be tapered so that the entrance diameter is smaller than the diameter of the aspiration channel 52. Laser energy delivered within the aspiration channel's 52 entrance can then be used to prevent unwanted clogging within the aspiration channel 52. It may also be advantageous to advance the fiber directly outside the channel in the unobstructed situation, where the smaller diameter fiber can be used as a sculpting or high precision disruption tool while the aspiration channel 52 pressure or flow is set to almost nothing. But during high flow aspiration modes, the laser is not required to disrupt tissue in the unobstructed situation and Poiseuilles law will hold. By monitoring the pressure and flow parameters and their rates of change, it is possible to determine if an occlusion has occurred, see below.

With further reference to FIG. 3, insertion of an example device is disclosed. FIG. 3 illustrates the distal tip of the example instrument 54 in which the aspiration needle 13 and the optical fiber 12 are collinear and the entrance of the aspiration channel 52 is unobstructed. The pressure within the aspiration channel 52 is low, and the flow rate is not limited by the pressure. In this example, the fiber tip 16 position is not critical and can be retracted by several mm within the aspiration needle. In some examples, the fiber tip 16 can be retracted up to and including a range of about 5 mm distally and up to and including a range of about 10 mm proximally. Other distances may be possible according to the dimensions of the human eye, and depending on the specific application. The laser energy used in a retracted position helps further disrupt tissue fragments that are drawn by negative pressure into the aspiration channel 52. In this mode the instrument 54 acts much like a conventional aspiration/irrigation instrument tip. Aspiration of the lens capsule is less likely to make contact with the fiber optic and can be preserved upon accidental aspiration.

It may be desirable within the surgical procedure to hold onto a piece of tissue with the aspiration needle until it is positioned appropriately within the anterior chamber for energetic disruption. Once a piece has been engaged with the aspiration pressure it may fill the entrance of the aspiration channel 52 and block further removal without increased pressure.

FIG. 4 illustrates such an example occlusion that occurs when the fiber is retracted. A fragment of tissue 81 is pulled towards the aspiration channel 52 by negative pressure, and is too large to be aspirated and completely occludes the aspiration channel 52 entrance. In this example situation, the pressure inside the aspiration channel 52 rises as a function of the flow rate and it is advantageous to advance the laser fiber towards the entrance of the aspiration channel 52 to disrupt tissue causing the obstruction, rather than to attempt aspiration at higher pressures.

Further, in this example embodiment, the aspiration needle is able to hold the occlusion better if the fiber is not protruding, otherwise the fiber itself becomes either buried inside the occluding tissue fragment, or prevents any occlusion from occurring. The tissue fragment is held to the tip of the aspiration needle by a force caused by the pressure difference between the fluid around the tissue fragment and the inside of the aspiration channel 52. In this case the relationship between pressure and flow rate deviates drastically from Poiseuilles law because Q approaches 0, since no volume can flow through the occlusion, assuming that R, and L are fixed.

$$Q \propto \frac{\Delta p}{\eta} \qquad \text{(equation 1)}$$

The solution for Q=0 only occurs if Δp=0 (the pump is off and the piece cannot be held) or the viscosity effectively becomes infinite η→∞. As the pump continues to try and aspirate despite the blockage, the pressure becomes proportional to the control signal, and rises quickly to its limit.

$$\Delta p \propto A \text{ for } \Delta P < \Delta p_{max} \text{ or } \Delta p = \Delta p_{max}$$

The time required to reach the pressure limit is often referred to as the aspiration fluidic systems 'rise-time', τ.

By monitoring the pressure and flow over time, an algorithm can predict an occlusion if the flow rate is dropping while the pressure is rising. In other words, when unobstructed and below the pressure and flow limits the control signal and the aspiration rate are well defined.

$Q \propto A(\Delta p)$ and thus the rate of change of flow with control signal is well defined $$\frac{dQ}{dA} \propto \text{constant}$$

and the pressure can be described by equation 1.

However, when occluded, additional demands for flow, increasing A, result in no additional flow: Q=0 and $$\frac{dQ(A)}{dA} \to 0$$

becomes negligible. Subsequently the rate of change of the pressure to the control signal now becomes well defined $$\frac{d\Delta p}{dA} = \text{constant.}$$

In this way the level of occlusion can be sampled by seeing how the flow rate and pressure react to changes in the control signal.

Assuming that while the occlusion occurs the control signal does not change:

$$\frac{dA}{dt} = 0.$$

Before the occlusion the tip is unobstructed and the flow rate is fixed by the control signal, and from equation 1 $\Delta p \propto Q \eta \propto A$ or $$\frac{d\Delta p}{dQ} \propto \eta > 0. \quad \text{(equation 2)}$$

However, once the occlusion occurs, the viscosity becomes effectively infinite as the initial flow rate $Q_0$ begins to drop to zero and $$\frac{dQ}{dt}$$

becomes negative and Δp grows over the 'rise time' to $\Delta p_{max}$. In other words, during this time, the sign of $$\frac{d\Delta p}{dQ} = \frac{(\Delta p_t \cdot \Delta p_0)}{(0 - Q_0)} < 0$$

changes and becomes negative. Meanwhile, the pressure begins to rise at the following rate, $$\frac{dP}{dt} = \frac{\Delta p_{max} \cdot \Delta p}{\tau}.$$

After the rise time the pressure is at its maximum value and neither flow nor pressure can change. In this case $$\frac{dQ}{dt} = 0, \frac{d\Delta p}{dt} = 0,$$

but now Q=0 AND $\Delta p = \Delta p_{max}$ so the pipe must be occluded completely. In other words, $$\left(\frac{d\Delta p}{dQ}\right)$$

becomes ill defined when fully occluded, but swings from positive when unobstructed, to negative during the 'rise' time.

In this example embodiment, a conventional phaco machine operator would begin to use higher vacuum pressures or ultrasound to disrupt the occlusion.

FIG. 5 discloses a means through which the laser fiber aids the transition from occluded to unobstructed. In other words, FIG. 5 discloses tissue fragment as it is disrupted and aspirated, and the occlusion is partially or completely cleared, and the laser fiber can begin to retract until another occlusion occurs. Once the occlusion begins to clear and the pressure no longer increases dramatically with the flow rate, the laser power can be reduced or the laser tip can be retracted to prevent the remaining tissue fragment from being pushed away from the tip. The greater the occlusion, the closer the fiber should be to the blocked entrance of the aspiration channel 52.

In some examples, a simple control algorithm can be defined to determine the position of the fiber tip based only on the pressure as follows:

$$D(t) \propto Dmax\left(1 - \frac{\Delta p(t)}{\Delta p_{max}}\right)max$$

D is a distance from the fiber tip to the aspiration channel 52 entrance.

In some examples, the fiber position can be set by the flow rate:

$$D(t) \propto Dmax * \frac{Q(t)}{Q_{max}}$$

In some examples, the fiber position can be determined by the relative change of pressure and flow:

$$D(t) \propto \frac{d}{dt}\left(\frac{d\Delta p}{dQ}\right)$$

In some examples, the fiber position can be simply linked to the user control signal that normally only controls the aspiration assuming that the user demand for higher aspiration will require laser assistance and hence a lower value for D.

$$D(t) \propto 1-A(t).$$

The above example algorithms are not meant to be limiting. Other example control algorithms may be possible.

FIG. 6 discloses a situation in which an occlusion is persistent and cannot be cleared within a certain time t>>τ. In this case the fiber position can be made to oscillate longitudinally within the channel, so as to increase the effective range of the high precision laser disruption and add a mechanical enhancement to the effect (similar to wiggling the tissue). In this example case, the control algorithm can assume that if the foot pedal is fully depressed for longer than a set time much greater than the rise time and the pressure is still at max, movement of the optical fiber is changed to oscillation mode. This is because extended input to aspirate while the pressure is not decreased may indicate that the occlusion has not been cleared and more mechanical assistance is needed.

In a further example embodiment, both laser pulse rate, envelope and fiber position are used to minimize total flow and pressure changes within the anterior capsule to achieve the most minimally invasive tissue removal possible and most importantly protect unintentional disruption of the capsule, or damage to corneal endothelial cells by laser energy, mechanical forces, or fluidics. The average power of the laser pulse is a function of the pulse rate and energy per pulse. Given a certain laser intensity threshold for laser tissue disruption it is useful to maintain a constant pulse energy and attenuate the laser power through reduction of the pulse rate rather than attenuation of the laser power. In the present disclosure, enhancement of the action of the instrument 54 occurs when the laser pulse rate is not evenly divided, but instead there is a time period in which the laser action is modulated by a lower frequency envelope. Envelope frequencies around 5 Hz have been found to be suitable in hardened eye tissue. Pulse rate can be increased or decreased from near 0-100% pulse width modulation of the laser pulses at the envelope frequency.

It is hypothesized that the laser pulse super heats a volume of tissue/liquid at the fiber tip. Since the tip is hard and the area (about 200 μm) is much larger than the depth of absorption (about 1 μm), the irradiated matter cannot expand backwards into the solid fiber and there is a net force pushing tissue away from the fiber. This expansion force causes an increase in pressure that counter-acts the vacuum pressure of the aspiration pump. By pausing the laser for some time during an occlusion, the aspiration pump can build a higher pressure, and the pressure change caused by the laser pulses are less likely to build up enough to reverse the sign of the pressure in the aspiration channel (and cause the tissue to detach).

With reference to FIG. 7, in some examples, the distal end of the fiber 16 can be set inside the aspiration needle 13 in such a way that the aspirated fluid 72 can be contained within a sterilizable or single use tool assembly 19, and does not contaminate some reusable portion of the fiber optic beam delivery 12 while allowing the non-elastic fiber optic to be moved within the aspiration channel. In some examples, this can be accomplished by means of a compressed rubber seal 73 within which the fiber is fixed in a moving shaft assembly 74. The tool assembly 19 contains irrigation 70 and aspiration 71 channels that connect to the distal tip and to tubing connectors with which to flexibly attach the means of fluidics control.

Figure 8:
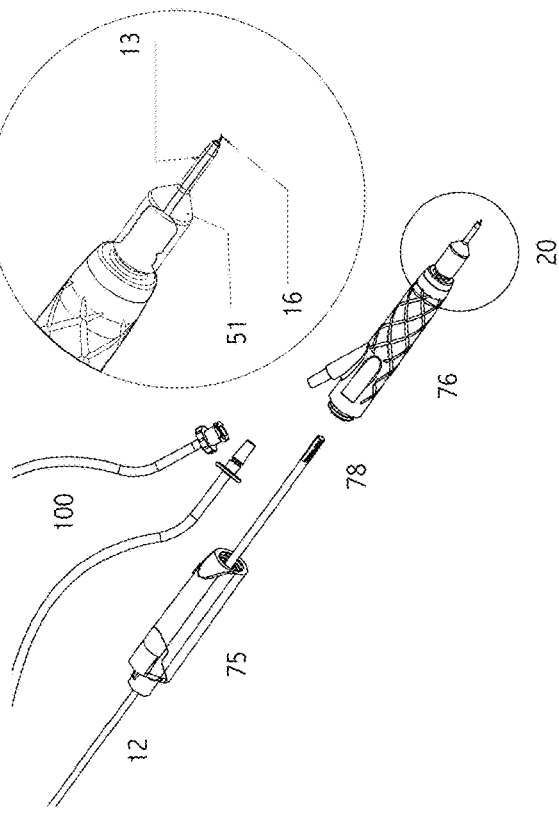
FIG. 8 is an example embodiment of the laser instrument of FIG. 2, where the instrument is shown as three separable parts: a re-useable laser delivery assembly, which includes a fiberoptic, that has a fiber connector, a detachable tip handle assembly, that includes a distal instrument tip, with an output channel for irrigation, aspiration needle, and extension fiber optic tip that also includes points for connecting disposable tubing to a disposable means of aspiration and irrigation.

With reference to FIG. 8, in some examples the instrument 54 comprises three separable parts: a re-useable laser delivery assembly 75, (which includes a fiberoptic 12 and that has a fiber connector 78); a detachable tip handle assembly 76, (that includes a distal instrument tip 20, with an output channel for irrigation 51 aspiration needle 13 and an extension fiber optic tip 16 that couples on its sagittal end to the re-useable delivery system's fiber connector 78); and a disposable means of aspiration and irrigation 100. Connection points for connecting the disposable tubing 100 to the tip handle assembly 76 may be provided or the two disposable parts may be pre-assembled.

Figure 9:
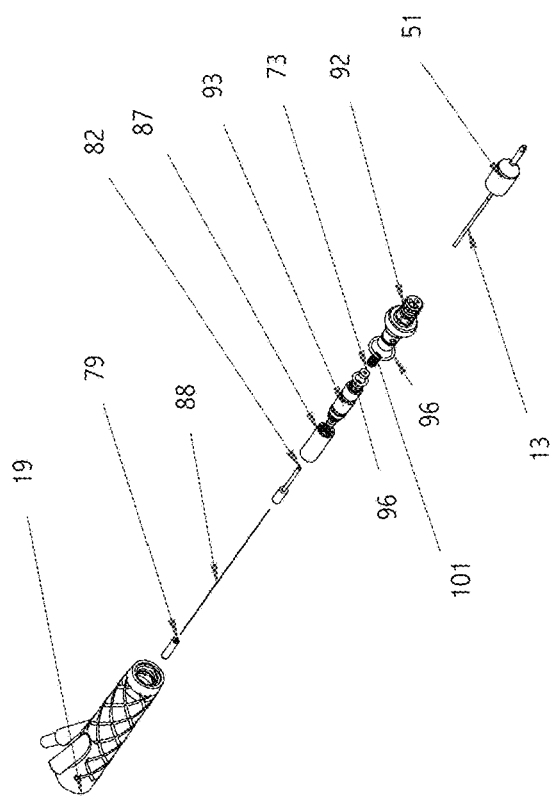
FIG. 9 is an example of an exploded view of a replaceable handle assembly in which a small optical fiber is attached to a fiber connector, which connects with the corresponding connector, of the reusable laser delivery assembly.

With reference to FIG. 9, an exploded view of a replaceable handle assembly 76 is disclosed. A small optical fiber 88 is attached to a fiber connector 79, which connects with the corresponding connector 78 of the reusable laser delivery assembly. A shaft assembly 82 allows the fiber optic to be sealed with a washer 73 that is compressed around the shaft assembly 82 by a threaded nut 87. The threaded nut 87 is held captive by the shaft assembly along with a spring 101 that acts to retract the fiber tip when not connected to the reusable portion of the assembly. A manifold 92 onto which the aspiration needle 13 and distal irrigation sleeve 51 are placed is coupled to the irrigation 70 and aspiration channels 71 of the handle assembly 19 via a manifold extension 93 and sealing washers 96 to keep the channels separated. The fiber shaft assembly attaches to the manifold extension 93 by the shaft sealing nut 87.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the disclosure has been presented to illustrate the principles of the disclosure and not to limit the disclosure to the particular embodiment illustrated. It is intended that the scope of the disclosure be defined by all of the embodiments encompassed within the following claims and their equivalents.

The invention claimed is:

1. An apparatus for disruption of cataracts in lens tissue comprising:
   a housing;
   a source of pulsed laser radiation;
   an optical waveguide at least partially housed within the housing, the optical waveguide including a flexible optical fiber, the optical waveguide being configured to transmit the pulsed laser radiation for causing disruption of cataracts, the optical waveguide being coupleable to the source of pulsed laser radiation at a proximal end of the optical waveguide to receive the pulsed laser radiation from the source of pulsed laser radiation;

at least one of a flow rate sensor or a pressure sensor positioned within aspiration and irrigation channels of the apparatus, at least one of the flow rate sensor or the pressure sensor being coupled to a control system; and a driving mechanism coupled to the optical waveguide for controllably changing the position of the optical waveguide relative to a distal end of the housing, the driving mechanism being controlled by the control system to position the optical fiber in response to at least one of a vacuum pressure from the pressure sensor or a flow rate from the flow rate sensor received by the control system.

2. The apparatus of claim 1, wherein the driving mechanism is controlled by the control system to position the optical fiber proportional to an aspiration level of tissue.

3. The apparatus of claim 1, further comprising a sensor configured to sense contact between the optical fiber and tissue.

4. The apparatus of claim 1, further comprising a photoacoustics sensor to sense a position of the optical fiber.

5. The apparatus of claim 1, further comprising an encoder to sense a position of the optical fiber.

6. The apparatus of claim 1, wherein the driving mechanism is controlled by the control system to oscillate the optical fiber longitudinally within the housing.

7. The apparatus of claim 1, wherein a pulse rate of the laser radiation is modulated by a selected frequency, thereby enabling laser power balanced with vacuum rates.

8. The apparatus of claim 1, wherein the optical fiber is made of a material selected from: sapphire, diamond, ZBLAN, or YAG.

9. The apparatus of claim 1, wherein a distal end of the optical fiber is curved, tapered or angled.

10. The apparatus of claim 1, wherein the optical fiber is made from an infrared-transmitting optical material.

11. The apparatus of claim 1, wherein the driving mechanism is a linear motor, a linear translation mechanism driven by a rotating motor, or a voice-coil actuator.

12. The apparatus of claim 1, wherein the housing comprises a re-useable laser delivery portion through which the optical fiber extends, and a detachable tip handle from which a fiber optic tip extends, the detachable tip handle being releasably securable to the re-useable laser delivery portion.

13. The apparatus of claim 12, wherein the optical fiber has a distal end with a fiber connector, and the fiber optic tip has a proximal end that couples with the fiber connector.

* * * * *